(12) United States Patent
Hunter et al.

(10) Patent No.: US 6,908,911 B1
(45) Date of Patent: *Jun. 21, 2005

(54) ANTIBACTERIAL AGENTS

(75) Inventors: Michael George Hunter, Cowley (GB); Raymond Paul Beckett, Cowley (GB); John Martin Clements, Cowley (GB); Mark Whittaker, Cowley (GB); Stephen John Davies, Cowley (GB); Lisa Marie Pratt, Cowley (GB); Zoe Marie Spavold, Cowley (GB); Steven Launchbury, Cowley (GB)

(73) Assignee: British Biotech Pharmaceuticals Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/049,274

(22) PCT Filed: Aug. 10, 1999

(86) PCT No.: PCT/GB99/02629

§ 371 (c)(1),
(2), (4) Date: Sep. 5, 2002

(87) PCT Pub. No.: WO01/10835

PCT Pub. Date: Feb. 15, 2001

(51) Int. Cl.[7] .................. A61K 31/33; A61K 31/19; A61K 31/16
(52) U.S. Cl. ............... 514/183; 514/1.19; 514/408; 514/247; 514/252.12; 514/212.01; 514/575; 540/484; 546/184; 544/358; 544/336
(58) Field of Search ................. 514/183, 1, 19, 514/408, 247, 252.12, 212.01, 575; 540/484; 546/184; 544/358, 336; 548/400

(56) References Cited

U.S. PATENT DOCUMENTS

| 4,996,358 A | * | 2/1991 | Handa et al. | ........... 562/621 |
| 6,423,690 B1 | * | 7/2002 | Hunter et al. | ........... 514/19 |
| 6,441,042 B1 | * | 8/2002 | Hunter et al. | ........... 514/575 |

FOREIGN PATENT DOCUMENTS

| WO | 9407527 | * | 4/1994 |
| WO | 9410990 | * | 5/1994 |
| WO | 94/10990 | | 5/1994 |
| WO | 9738705 | * | 10/1997 |
| WO | 99/39704 | | 8/1999 |

OTHER PUBLICATIONS

Fournie–Zaluski et al, J. Med. Chem. 28, 1158–69(1985).*
Y.Jin et al, "Inhibition Stereochemistry of hydroxamate inhibitors for thermilysin", Bioorganic Medicinal Chem. Letters,GB,Oxford,8/24,3515–18(1998).*
Foutnie–Saluski et al,"New Bidentase as full inhibitors of enkephalin–degrading enzymes:synthesis and analgesis properties", J Med. Chem. USA 28/9, 1158–69(1985).*
PubMed Abstract 15032731, also cited as Curr. Med. Chem. 11/6,775–93(2004).*
PunMed Abstract 14973152, also cited as J. Antimicrob. Chemther. 53/4,664–8(2004).*
PubMed Abstracts 14963065, also cited as J. Antimicrob. Chemther. 53/3,487–93(2004).*
PubMed Abstract 14693547, also cited as Antimicrob. Agents Chemther. 48/1, 250–61(2004).*
PubMed Abstract 12183225, also cited as Antimicrob, Agents Chemther. 46/9,2752–64(2002).*
Weller et al,Biochem. & Biophy. Res. Communic. 125/1, 82–89(1984).*
Fournie–Saluski M–C, et al.: "New Bidentases as full inhibitors of enkephalin–degrading enzymes: synthesis and analgesis properties", Journal of Medicinal Chemistry, US, American Chemical Society, Washington, vol. 28, No. 9, Jan. 1, 1985, pp. 1158–1169, XP002019770.
Y Jin, et al.: "Inhibition stereochemistry of hydroxamate inhibitors for thermolysin", Biooranic Medicinal Chemistry Letters, GB, Oxford, vol. 8, No. 24, 1998, pp. 3515–3518, XP002106374.

* cited by examiner

Primary Examiner—Richard L. Raymond
Assistant Examiner—Sudhaker B. Patel
(74) Attorney, Agent, or Firm—Banner & Witcoff Ltd.

(57) ABSTRACT

Selected compounds of formula (I) are antibacterial agents: formula (I) wherein $R_2$ represents a substituted or unsubstituted $C_1$–$C_6$ alkyl, cycloalkyl ($C_1$–$C_6$ alkyl)- or aryl ($C_1$–$C_6$ alkyl)-group, and A represents a group of formula (IA), or (IB) wherein $R_4$ represents the side chain of a natural or non-natural alpha amino acid, and $R_5$ and $R_6$ are each independently hydrogen or $C_1$–$C_6$ alkyl, heterocyclic or aryl ($C_1$–$C_6$ alkyl)-, $R_5$ and $R_6$ when taken together with the nitrogen atom to which they are attached from an optionally substituted saturated heterocyclic ring of 3 to 8 atoms which ring is optionally fused to a carbocyclic or second heterocyclic ring

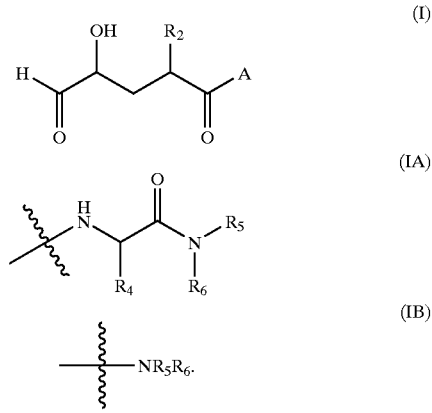

2 Claims, No Drawings

ANTIBACTERIAL AGENTS

This is a U.S. National Phase Application Under 35 USC 371. Applicants herewith claim the benefit of PCT/GB99/02629 filed Aug. 10, 1999, which was published Under PCT Article 21(2) in English on Feb. 15, 2001.

This invention relates to the use of N-formyl hydroxylamine derivatives as antibacterial agents, to a novel class of such compounds, and to pharmaceutical and veterinary compositions comprising such compounds.

BACKGROUND TO THE INVENTION

In general, bacterial pathogens are classified as either Gram-positive or Gram-negative. Many antibacterial agents (including antibiotics) are specific against one or other Gram-class of pathogens. Antibacterial agents effective against both Gram-positive and Gram-negative pathogens are therefore generally regarded as having broad spectrum activity.

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as *Staphylococci, Streptococci, Mycobacteria* and *Enterococci*, resistant strains have evolved/arisen which makes them particularly difficult to eradicate. Examples of such strains are methicillin resistant *Staphylococcus aureus* (MRSA), methicillin resistant coagulase negative *Staphylococci* (MRCNS), penicillin resistant *Streptococcus pneumoniae* and multiply resistant *Enterococcus faecium*.

Pathogenic bacteria are often resistant to the aminoglycoside, β-lactam (penicillins and cephalosporins), and chloramphenicol types of antibiotic. This resistance involves the enzymatic inactivation of the antibiotic by hydrolysis or by formation of inactive derivatives. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of *enterococci* (Woodford N. 1998 Glycopeptide-resistant *enterococci*: a decade of experience. Journal of Medical Microbiology. 47(10):849–62). Vancomycin-resistant *enterococci* are particularly hazardous in that they are frequent causes of hospital based infections and are inherently resistant to most antibiotics. Vancomycin works by binding to the terminal D-Ala-D-Ala residues of the cell wall peptidioglycan precursor. The high-level resistance to vancomycin is known as VanA and is conferred by a genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant *enterococci* and β-lactam antibiotic-resistant bacteria, such as methicillin-resistant *Staphylococcus aureus*, is of utmost importance.

BRIEF DESCRIPTIONS OF THE INVENTION

This invention is based on the finding that certain N-formyl hydroxylamine derivatives have antibacterial activity, and makes available a new class of antibacterial agents. The inventors have found that the compounds with which this invention is concerned are antibacterial with respect to a range of Gram-positive and Gram-negative organisms.

Although it may be of interest to establish the mechanism of action of the compounds with which the invention is concerned, it is their ability to inhibit bacterial growth that makes them useful. However, it is presently believed that their antibacterial activity is due, at least in part, to intracellular inhibition of bacterial polypeptide deformylase (PDF; EC 3.5.1.31).

All ribosome-mediated synthesis of proteins starts with a methionine residue. In prokaryotes the methionyl moiety carried by the initiator tRNA is N-formylated prior to its incorporation into a polypeptide. Consequently, N-formylmethionine is always present at the N-terminus of a nascent bacterial polypeptide. However, most mature proteins do not retain the N-formyl group or the terminal methionine residue. Deformylation is required prior to methionine removal, since methionine aminopeptidase does not recognise peptides with an N-terminal formylmethionine residue (Solbiati et al., J. Mol. Biol. 290:607–614, 1999). Deformylation is, therefore, a crucial step in bacterial protein biosynthesis and the enzyme responsible, PDF, is essential for normal bacterial growth. Although the gene encoding PDF (def) is present in all pathogenic bacteria for which sequences are known (Meinnel et al., J. Mol. Biol, 266:93949, 1997), it has no eukaryotic counterpart, making it an attractive target for antibacterial chemotherapy.

The isolation and characterisation of PDF has been facilitated by an understanding of the importance of the metal ion in the active site (Groche et al., Biophys. Biochem. Res. Commun., 246:324–6, 1998). The $Fe^{2+}$ form is highly active in vivo but is unstable when isolated due to oxidative degradation (Rajagopalan et al., J. Biol. Chem. 273:22305–10, 1998). The $Ni^{2+}$ form of the enzyme has specific activity comparable with the ferrous enzyme but is oxygen-insensitive (Ragusa et al., J. Mol. Biol. 1998, 280:515–23, 1998). The $Zn^{2+}$ enzyme is also stable but is almost devoid of catalytic activity (Rajagopalan et al., J. Am. Chem. Soc. 119:12418–12419, 1997).

Several X-ray crystal structures and NMR structures of *E. coli* PDF, with or without bound inhibitors, have been published (Chan et al., Biochemistry 36:13904–9, 1997; Becker et al., Nature Struct. Biol. 5:1053–8, 1998; Becker et al., J. Biol. Chem. 273:11413–6, 1998; Hao et al., Biochemistry, 38:4712–9, 1999; Dardel et al., J. Mol. Biol. 280:501–13, 1998; O'Connell et al., J. Biomol. NMR, 13:311–24, 1999), indicating similarities in active site geometry to metalloproteinases such as thermolysin and the metzincins.

Recently the substrate specificity of PDF has been extensively studied (Ragusa et al., J. Mol. Biol. 289:1445–57, 1999; Hu et al., Biochemistry 38:643–50, 1999; Meinnel et al., Biochemistry, 38:4287–95, 1999). These authors conclude that an unbranched hydrophobic chain is preferred at P1', while a wide variety of P2' substituents are acceptable and an aromatic substituent may be advantageous at the P3' position. There have also been reports that small peptidic compounds containing an H-phosphonate (Hu et al., Bioorg. Med. Chem. Lett., 8:2479–82, 1998) or thiol (Meinnel et al., Biochemistry, 38:4287–95, 1999) metal binding group are micromolar inhibitors of PDF. Peptide aldehydes such as calpeptin (N-Cbz-Leu-norleucinal) have also been shown to inhibit PDF (Durand et al., Arch. Biochem. Biophys., 367:297–302, 1999). However, the identity of the metal binding group and its spacing from the rest of the molecule ("recognition fragment") has not been studied extensively. Furthermore, non-peptidic PDF inhibitors, which may be desirable from the point of view of bacterial cell wall permeability or oral bioavailability in the host species, have not been identified.

RELATED PRIOR ART

Certain N-formyl hydroxylamine derivatives have previously been claimed in the patent publications listed below, although very few examples of such compounds have been specifically made and described:

| | |
|---|---|
| EP-B-0236872 | (Roche) |
| WO 92/09563 | (Glycomed) |
| WO 92/04735 | (Syntex) |
| WO 95/19965 | (Glycomed) |
| WO 95/22966 | (Sanofi Winthrop) |
| WO 95/33709 | (Roche) |
| WO 96/23791 | (Syntex) |
| WO 96/16027 | (Syntex/Agouron) |
| WO 97/03783 | (British Biotech) |
| WO 97/18207 | (DuPont Merck) |
| WO 98/38179 | (GlaxoWellcome) |
| WO 98/47863 | (Labs Jaques Logeais) |

The pharmaceutical utility ascribed to the N-formyl hydroxylamine derivatives in those publications is the ability to inhibit matrix metalloproteinases (MMPs) and in some cases release of tumour necrosis factor (TNF), and hence the treatment of diseases or conditions mediated by those enzymes, such as cancer and rheumatoid arthritis. That prior art does not disclose or imply that N-formyl hydroxylamine derivatives have antibacterial activity.

In addition to these, U.S. Pat. No. 4,738,803 (Roques et al.) also discloses N-formyl hydroxylamine derivatives, however, these compounds are disclosed as enkephalinase inhibitors and are proposed for use as antidepressants and hypotensive agents. Also, WO 97/38705 (Bristol-Myers Squibb) discloses certain N-formyl hydroxylamine derivatives as enkephalinase and angiotensin converting enzyme inhibitors. This prior art does not disclose or imply that N-formyl hydroxylamine derivatives have antibacterial activity either.

Our copending International Patent Application No. PCT/GB99/0386 describes and claims, inter alia, the use of a compound of formula (I) or a pharmaceutically or veterinarily acceptable salt thereof in the preparation of an antibacterial composition:

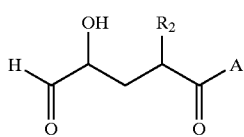
(I)

wherein $R_2$ represents a substituted or unsubstituted $C_1$–$C_6$ alkyl, cycloalkyl($C_1$–$C_6$ alkyl)-, or aryl($C_1$–$C_6$ alkyl)-group, and A represents a group of formula (IA), or (IB):

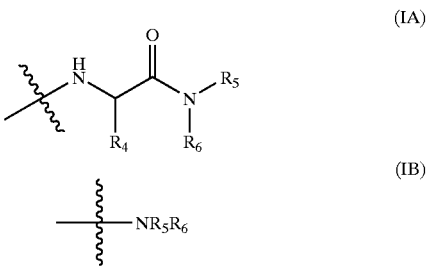

wherein $R_4$ represents the side chain of a natural or non-natural alpha amino acid, and $R_5$ and $R_6$ are each independently hydrogen or $C_1$–$C_6$ alkyl, heterocyclic or aryl($C_1$–$C_6$ alkyl), or $R_5$ and $R_6$ when taken together with the nitrogen atom to which they are attached form an optionally substituted saturated heterocyclic ring of 3 to 8 atoms which ring is optionally fused to a carbocyclic or second heterocyclic ring.

DETAILED DESCRIPTION OF THE INVENTION

The present invention provides additional members of the class of compounds disclosed in PCT/GB99/00386, but which were not specifically identified or exemplified therein. As members of the class disclosed in PCT/GB99/00386, the present compounds are antibacterially active, and their mechanism of action is presently believed to be due at least in part to their ability to inhibit bacterial peptide deformylases.

Accordingly, the present invention provides a compound of formula (I) as defined above, selected from the group consisting of:

N-[3S-(4-benzylpiperidine-1-carbonyl)-2,2-dimethyl-propyl]3-cyclopentyl-2R-[(formyl-hydroxy-amino)-methyl]-propionamide, N-[2R-(4-benzyl-piperidine-1-carbonyl)-hexyl]-N-hydroxy-formamide, N-hydroxy-N-[2R-(2-methyl-piperidine-1-carbonyl)-hexyl]-formamide, N-hydroxy-N-[2R-piperidine-1-carbonyl)-hexyl]-formamide, N-hydroxy-N-[2R-(piperazine-1-carbonyl)-hexyl]-formamide, 2R-[(formyl-hydroxy-amino)-methyl]-hexanoic acid pyrrolidin-1-ylamide, 2R-[(formyl-hydroxy-amino)-methyl]-hexanoic acid methyl-1-methyl-piperidin-4-yl)-amide, N-[2R-(azepane-1-carbonyl)-hexyl]-N-hydroxy-formamide, 2R-[(formyl-hydroxy-amino)-methyl]-hexanoic acid (4-methyl-piperazin-1-yl)-amide, 2R-[(formyl-hydroxy-amino)-methy]-hexanoic acid diisopropylamide, 1-{2R-[(formyl-hydroxy-amino)-methyl]-hexanoyl}-piperidine-3-carboxylic acid ethyl ester, 4-{2R-[(formyl-hydroxy-amino)-methyl]-hexanoyl}-piperazine-1-carboxylic acid ethyl ester, 4-{2R-[(formyl-hydroxy-amino)-methyl]-hexanoyl}-1,1-dimethyl-piperazinium iodide, 2R-[(Formyl-hydroxy-amino)-methyl]-hexanoic acid [2,2-dimethyl-1S-(piperidine-1 carbonyl)-propyl]-amide, 2R-[(formyl-hydroxy-amino)-methyl]-hexanoic acid [1S-(3,
4-dihydro-1H-isoquinoline-2-carbonyl)-2,2-dimethyl-
propyl]-amide,
2R-[(formyl-hydroxy-amino)-methyl]-hexanoic acid [1S-
(4-benzyl-4-hydroxy-piperidine-1-carbonyl)-2,2-
dimethyl-propyl]-amide,
2R-[(formyl-hydroxy-amino)-methyl]-hexanoic acid [1S-
(4-benzyl-piperazine-1-carbonyl)-2,2-dimethyl-propyl]-
amide,
2R-[(formyl-hydroxy-amino)-methyl]-hexanoic acid
(3-benzylsulfanyl-1S-dimethylcarbamoyl-propyl)-amide,
3S-{2R-[(formyl-hydroxy-amino)-methyl]-
hexanoylamino}-N,N-dimethyl-succinamic acid benzyl
ester,
4S-dimethylcarbamoyl-4-{2R-[(formyl-hydroxy-amino)-
methyl]-hexanoyl-amino}-butyric acid benzyl ester,
(5S-dimethylcarbamoyl-5-{2R-[(formyl-hydroxy-amino)-
methyl]-hexanoyl-amino}-pentyl)-dimethyl-ammonium
chloride,
2R-[(formyl-hydroxy-amino)-methyl]butyric acid
(1-carbamoyl-2,2-dimethyl-propyl)amide,
2-[(formyl-hydroxy-amino)-methyl]-hexanoic acid
(1-carbamoyl-2,2-dimethyl-propyl)amide,
2R-[formyl-hydroxy-amino)-methyl]-hexanoic acid
(1-dimethyl-carbamoyl-4-guanidinobutyl)-amide,
2R-[2-(4-chlorophenyl)-3-(formyl-hydroxy-amino)-
propionylamino]-2S-3,3,N,N-tetramethyl-butyramide,
2R-[(formyl-hydroxy-amino)-methyl]-hexanoic acid [2(3,4-
dihydroxy-phenyl)-ethyl]-amide,
2R-[(formyl-hydroxy-amino)-methyl]-hexanoic acid [2(4-
hydroxyphenyl)-ethyl]-amide,
and pharmacetically and veterinarily acceptable salts,
hydrates and solvates thereof.

According to other aspects of the invention, there is
provided (a) the use of a compound specifically named
immediately above, or a pharmaceutically or veterinarily
acceptable salt solvate or hydrate thereof, in the preparation
of an antibacterial composition; (b) a method for the treat-
ment of bacterial infections in humans and non-human
mammals, which comprises administering to a subject suf-
fering such infection an antibacterially effective dose of a
compound specifically named immediately above, or a phar-
maceutically or veterinarily acceptable salt solvate or
hydrate thereof; (c) a method for the treatment of bacterial
contamination by applying an antibacterially effective
amount of a compound specifically named immediately
above, or a pharmaceutically or veterinarily acceptable salt
solvate or hydrate thereof, to the site of contamination; and
(d) a pharmaceutical or veterinary composition comprising
a compound specifically named immediately above, or a
pharmaceutically or veterinarily acceptable salt solvate or
hydrate thereof, together with a pharmaceutically or veteri-
narily acceptable carrier.

Of the compounds of the invention, the following are
presently especially preferred for their potency as antibac-
terial agents:
N-[3S-(4-benzylpiperidine-1-carbonyl)-2,2-dimethyl-
propyl]-3-cyclopentyl-2R-[(formyl-hydroxy-amino)-
methyl]-propionamide,
2R-[(formyl-hydroxy-amino)-methyl]-hexanoic acid
methyl-(1-methyl-piperidin 4-yl)-amide,
2R-[(formyl-hydroxy-amino)-methyl]-hexanoic acid [1S-
(4-benzyl-4-hydroxy-piperidine-1-carbonyl)-2,2-
dimethyl-propyl]-amide,
2R-[(formyl-hydroxy-amino)-methyl]-hexanoic acid [1S-
(4-benzyl-piperazine-1-carbonyl)-2,2-dimethyl-propyl]-
amide,
2R-[(formyl-hydroxy-amino)-methyl]-hexanoic acid
(3-benzylsulfanyl-1S-dimethylcarbamoyl-propyl)-amide,
and
2-[(formyl-hydroxy-amino)-methyl]-hexanoic acid
(1-carbamoyl-2,2-dimethyl-propyl)amide.

On the hypothesis that the compounds (I) act by inhibition
of intracellular PDF, the most potent antibacterial effect may
be achieved by using compounds which efficiently pass
through the bacterial cell wall. Thus, compounds which are
highly active as inhibitors of PDF in vitro and which
penetrate bacterial cells are preferred for use in accordance
with the invention. It is to be expected that the antibacterial
potency of compounds which are potent inhibitors of the
PDF enzyme in vitro, but are poorly cell penetrant, may be
improved by their use in the form of a prodrug, ie a
structurally modified analogue which is converted to the
parent molecule of formula (I), for example by enzymic
action, after it has passed through the bacterial cell wall.

Salts of the compounds of the invention include physi-
ologically acceptable acid addition salts for example
hydrochlorides, hydrobromides, sulphates, methane
sulphonates, p-toluenesulphonates, phosphates, acetates,
citrates, succinates, lactates, tartrates, fumarates and male-
ates. Salts may also be formed with bases, for example
sodium, potassium, magnesium, and calcium salts.

Compositions with which the invention is concerned may
be prepared for administration by any route consistent with
the pharmacokinetic properties of the active ingredient(s).

Orally administrable compositions may be in the form of
tablets, capsules, powders, granules, lozenges, liquid or gel
preparations, such as oral, topical, or sterile parenteral
solutions or suspensions. Tablets and capsules for oral
administration may be in unit dose presentation form, and
may contain conventional excipients such as binding agents,
for example syrup, acacia, gelatin, sorbitol, tragacanth, or
polyvinyl-pyrrolidone; fillers for example lactose, sugar,
maize-starch, calcium phosphate, sorbitol or glycine; tablet-
ting lubricant, for example magnesium stearate, talc, poly-
ethylene glycol or silica; disintegrants for example potato
starch, or acceptable wetting agents such as sodium lauryl
sulphate. The tablets may be coated according to methods
well known in normal pharmaceutical practice. Oral liquid
preparations may be in the form of, for example, aqueous or
oily suspensions, solutions, emulsions, syrups or elixirs, or
may be presented as a dry product for reconstitution with
water or other suitable vehicle before use. Such liquid
preparations may contain conventional additives such as
suspending agents, for example sorbitol, syrup, methyl
cellulose, glucose syrup, gelatin hydrogenated edible fats;
emulsifying agents, for example lecithin, sorbitan
monooleate, or acacia; non-aqueous vehicles (which may
include edible oils), for example almond oil, fractionated
coconut oil, oily esters such as glycerine, propylene glycol,
or ethyl alcohol; preservatives, for example methyl or propyl
p-hydroxybenzoate or sorbic acid, and if desired conven-
tional flavouring or colouring agents.

For topical application to the skin, the active ingredient(s)
may be made up into a cream, lotion or ointment. Cream or
ointment formulations which may be used for the drug are
conventional formulations well known in the art, for
example as described in standard textbooks of pharmaceu-
tics such as the British Pharmacopoeia.

The active ingredient(s) may also be administered
parenterally in a sterile medium. Depending on the vehicle
and concentration used, the drug can either be suspended or
dissolved in the vehicle. Advantageously, adjuvants such as
a local anaesthetic, preservative and buffering agents can be dissolved in the vehicle. Intra-venous infusion is another route of administration for the compounds used in accordance with the invention.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples describe the preparation of the compounds of the invention. In the Examples, $^1$H and $^{13}$C NMR spectra were recorded using a Bruker DPX 250 spectrometer at 250.1 and 62.9 MHz, respectively. Mass spectra were obtained using a Perkin Elmer Sciex API 165 spectrometer using both positive and negative ionisation modes. Infra-red spectra were recorded on a Perkin Elmer PE 1600 FTIR spectrometer. The following abbreviations have been used throughout:

| | |
|---|---|
| DIAD | Diisopropylazodicarboxylate |
| DIPEA | Diisopropylethylamine |
| DMF | N,N-Dimethylformamide |
| EDC | 1-(3-Dimethylaminopropyl)-3-ethylcarbodiimide hydrochloride |
| HOAt | 1-Hydroxy-7-aza-benzotiazole |
| HOBt | 1-Hydroxybenzotriazole |
| LRMS | Low resolution mass spectrometry |
| THF | Tetrahydrofuran |

EXAMPLE 1

N-[3S-(4-Benzylpiperidine-1-carbonyl)-2,2-dimethyl-propyl]-3-cyclopentyl-2R-[(formyl-hydroxy-amino)-methyl]-propionamide

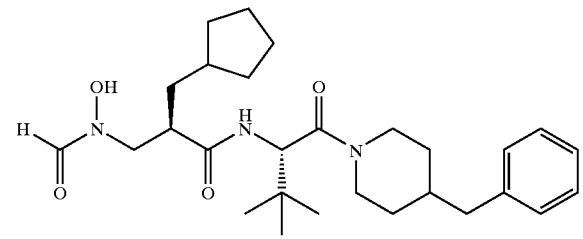

The title compound was prepared as detailed below (see also Scheme 1).

Scheme 1

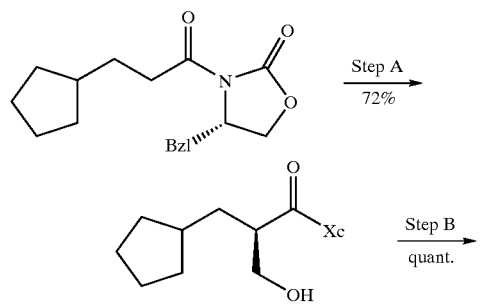

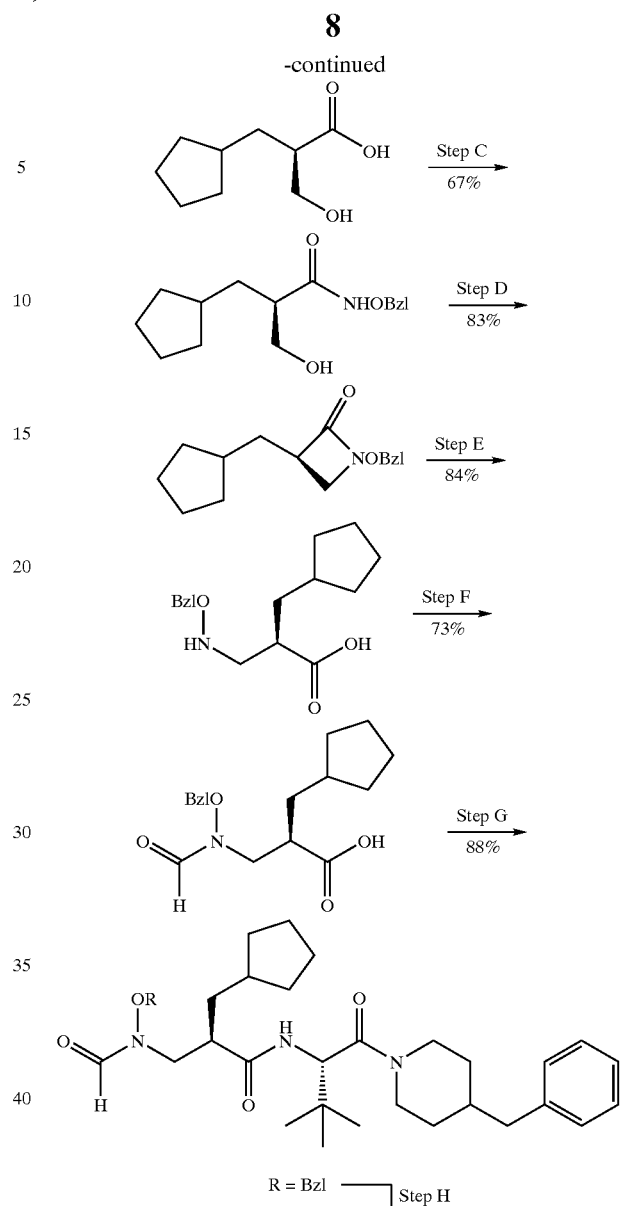

Reagents and Conditions: A: TiCl$_4$, trioxane, CH$_2$Cl$_2$; B: H$_2$O$_2$, LiOH; C: H$_2$NOBn, WSC, THF/H$_2$O; D: Ph$_3$P, DIAD, THF; E: LiOH, THF/MeOH/H$_2$O; F: formic acetic anhydride, NEt$_3$, THF; G: H-Tle-amide, EDCl, HOAt, DMF; H: Pd/C, H$_2$, MeOH.

Step A: 4S-Benzyl-3-[3-cyclopentyl-2R-hydroxymethyl-propionyl]-oxazolidin-2-one

To a stirred, cooled (0° C.) solution of 4S-benzyl-(3-cyclopentyl-propionyl)-oxazolidin-2-one (21 g, 69.8 mmol) in dichloromethane (350 ml) was added a solution of titanium tetrachloride (1M in dichloromethane, 73.25 ml, 73.2 mmol), dropwise. The resulting yellowish slurry was stirred for 10 minutes at 0° C., and then DIPEA (13.37 ml, 76.7 ml) was added dropwise to furnish a dark-red solution. The stirring was maintained for 1 h at 0° C., and then a solution of s-trioxane (7.53 g, 83.7 mmol), in dichloromethane (70 ml) was added dropwise followed by the addition of a solution of titanium tetrachloride (1M in dichloromethane, 73.25 ml, 73.2 mmol). The reaction mixture was then stirred for 4 h at 0° C. Saturated aqueous ammonium chloride (250 ml) was added to the reaction mixture and the aqueous layer was extracted with additional dichloromethane (2×300 ml).

The combined organic layers were washed with water (150 ml) and with brine (80 ml), dried over anhydrous magnesium sulfate, filtered and concentrated in vacuo to yield a yellow solid which on trituration with diethyl ether furnished a white solid (16.57 g, 72%). $^1$H-NMR; δ(CDCl$_3$), 7.38–7.22 (5H, m), 4.70 (1H, m), 4.22–4.18 (2H, m), 3.99 (1H, m), 3.96–3.75 (2H, m), 3.31 (1H, dd, J=13.4 & 3.3 Hz), 2.82 (1H, dd, J=13.4 & 9.4 Hz), 2.24 (1H, dd, J=8.3 & 4.5 Hz), 2.81–1.30 (4H, m) and 1.13 (1H, m); $^{13}$C-NMR; δ(CDCl$_3$), 176.3, 153.6, 135.2, 129.5, 129.0, 127.4, 66.2, 64.2, 55.7, 44.8, 37.9, 37.8, 34.6, 33.0, 32.4 and 25.1.

Step B: 3-Cyclopentyl-2R-hydroxymethyl-propionic Acid

To a stirred, cooled (0° C.) solution of 4S-Benzyl-3-[3-cyclopentyl-2R-hydroxymethyl-propionyl]-oxazolidin-2-one (16.05 g, 48.5 mmol) in THF-water (4:1, 250 ml) was added 27.5% aqueous hydrogen peroxide (24 ml, 194 mmol), followed by lithium hydroxide monohydrate (4.07 g, 97 mmol) in water (50 ml). After the reaction was complete (30 min), THF was removed in vacuo. The aqueous layer was extracted with dichloromethane (3×100 ml) and acidified to pH 2 with 4M hydrochloric acid. The aqueous layer was extracted with diethyl ether (2×150 ml). The combined organic layers were washed with brine (60 ml), dried over anhydrous magnesium sulfate and filtered. The solvent was removed in vacuo to afford a yellow oil which was further purified by column chromatography (25% ethyl acetate in hexanes to 100% ethyl acetate) to furnish the title compound as an oil (8.3 g, quant.). $^1$H-NMR; δ (CDCl$_3$), 6.60–5.90 (1H, br s), 3.80–3.78 (2H, m), 2.67 (1H, m), 1.98–1.40 (9H, m) and 1.20–0.98 (2H, m). $^{13}$C-NMR; δ(CDCl$_3$), 181.0, 63.2, 46.9, 37.8, 34.5, 32.7, 32.6, 25.1 and 25.1.

Step C: N-Benzyloxy-3-cyclopentyl-2R-hydroxymethyl-propionamide

To a stirred, cooled (0° C.) mixture of 3-cyclopentyl-2R-hydroxymethyl-propionic acid (1.1 g, 6.4 mmol) in THF-water (4:1, 30 ml), was added O-benzylhydroxylamine. The pH of the resulting solution was adjusted to 4.5 by addition of 1M hydrochloric acid, and then EDC (1.84 g, 9.6 mmol) was added in one portion. The resulting solution was stirred for 2.5 h at room temperature while controlling pH at 4.5 by addition of 1M hydrochloric acid. After removal of the THF, the aqueous layer was extracted with ethyl acetate (3×40 ml) and the combined organic layers were washed with 10% citric acid (3×15 ml), 5% sodium hydrogen carbonate and dried over anhydrous magnesium sulfate. The solvent was removed in vacuo to afford the title compound as a colourless crystalline solid (1.18 g, 67%). This compound was then used without any further purification. $^1$H-NMR; δ(CDCl$_3$), 8.14 (1H, br s), 7.40–7.34 (5H, m), 4.94 (2H, br s), 3.76–3.66 (2H, m), 1.79–1.47 (11H, m) and 1.17–0.97 (2H, m). LRMS: +ve ion 278 [M+H], 555 [2M+H].

Step D: N-Benzyloxy-3R-cyclopentylmethyl-azetidin-2-one

To a stirred, cooled (0° C.) solution of N-Benzyloxy-3-cyclopentyl-2R-hydroxymethyl-propionamide (8.63 g, 31.1 mmol) and triphenylphosphine (9 g, 34.2 mmol) in dry THF (320 ml) was added DIAD (6.12 ml, 31.1 mmol), dropwise. The resulting solution was stirred at room temperature overnight. After removal of THF in vacuo, the residue was purified by column chromatography (hexanes:ethyl acetate, 5:1 to 3:1) to give the desired product as a white solid (6.7 g, 83%). $^1$H-NMR; δ (CDCl$_3$), 7.76–7.39 (5H, m), 4.94 (2H, br s), 3.36 (1H, m), 2.96–2.80 (2H, m), 1.89–1.38 (9H, m) and 1.18–0.98 (2H, m). $^{13}$C-NMR; δ (CDCl$_3$), 167.7, 129.6, 129.3, 129.0, 78.1, 52.5, 45.1, 39.1, 35.2, 33.1, 32.9, 25.5 and 25.3. LRMS: +ve ion 260 [M+H], 519 [2M+H].

Step E: 2R-(Benzyloxyamino-methyl)-3-cyclopentyl-propionic Acid

To a stirred, cooled (0° C.) solution of N-Benzyloxy-3R-cyclopentylmethyl-azetidin-2-one (6.7 g, 25.8 mmol) in THF-methanol (3:1, 100 ml) was added lithium hydroxide monohydrate (1.3 g, 31.0 mmol) in water (25 ml). The reaction mixture was stirred and allowed to warm to room temperature overnight. The solvent was removed in vacuo and the aqueous layer was extracted with diethyl ether, then acidified to pH 2 by addition of 4M hydrochloric acid. The aqueous layer was extracted with diethyl ether (3×40 ml), and the combined organic layers were washed with brine, dried over anhydrous magnesium sulfate, filtered and concentrated in vacuo to give the title compound as white crystals (6.02 g, 84%). $^1$H-NMR; δ (CDCl$_3$), 7.68–7.30 (5H, m), 4.78–4.68 (2H, m), 3.12–3.10 (2H, d, J=6.9 Hz), 2.76 (1H, m), 1.91–1.39 (11H, m), 1.20–1.00 (2H, m). $^{13}$C-NMR: δ (CDCl$_3$), 180.1, 137.7, 129.0, 128.9, 128.5, 78.0, 53.9, 42.9, 38.3, 36.6, 33.1, 33.0, 25.5. LRMS: –ve ion 276 [M–H], 553 [2M–H].

Step F: 2R-[(Benzyloxy-formyl-amino)-methyl]-3-cyclopentyl-propionic Acid

To a stirred, cooled (0° C.) solution of 2R-(benzyloxyamino-methyl)-3-cyclopentyl propionic acid (3.79 g, 13.7 mmol) in THF (20 ml) was added formic acetic anhydride (3.01 g, 34.2 mmol) and triethylamine (5.72 ml, 41.0 mmol). The reaction mixture was stirred for 1 h at 0° C. and 45 min at room temperature. The solvent was removed in vacuo and the mixture was purified by flash chromatography (hexanes:ethyl acetate, 1:1) to give the title compound as a yellow oil (3.04 g, 73%). LRMS: –ve ion 304 [M–H], –ve ion 609 [2M–H].

Step G: 2R-[(Benzyloxy-formyl-amino)-methyl]-N-[1S-(4-benzyl-piperidine-1-carbonyl)-2,2-dimethyl-propyl]-3-cyclopentyl-propionamide To a stirred, cooled (0° C.) solution of 2R-[(Benzyloxy-formyl-amino)-methyl]-3-cyclopentyl-propionic acid (396 mg, 1.3 mmol) and 2S-Amino-1-(4-benzyl-piperidin-1-yl)-3,3-dimethyl-butan-1-one (see below) in DMF (5 ml), were added EDC (274 mg, 1.43 mmol) and HOAt (8.8 mg, 0.065 mmol). The reaction mixture was stirred overnight at room temperature. DMF was removed in vacuo to furnish a yellow oil, which was dissolved in ethyl acetate. The organic layer was then washed with 1M hydrochloric acid (2×5 ml) and water (5 ml). The aqueous layer was re-extracted with ethyl acetate. The combined organic layers were washed with brine, dried over anhydrous magnesium sulfate, filtered and the solvent was removed in vacuo to furnish a white foam (660 mg, 88%) which was used in the next step without any purification.

Step H: N-[1S-(4-benzylpiperidine-1-carbonyl)-2,2-dimethyl-propyl]-3-cyclopentyl-2R-[(formyl-hydroxy-amino)-methyl]-propionamide To a stirred solution of the 2R-[(benzyloxy-formyl-amino)-methyl]-N-[1 S-(4-benzylpiperidine-1-carbonyl)-2,2-dimethyl-propyl]-3-cyclopentyl-propionamide (655 mg, 1.14 mmol) in Methanol (8 ml) under an argon atmosphere was added Pd/C (70 mg). Hydrogen gas was bubbled through the suspension for 30 min. The reaction mixture was then filtered through celite and the solvent was removed in vacuo to afford a pale pink solid (522 mg, 95%). ¹H-NMR; δ (CDCl₃, rotamers), 8.40 (0.4H, m), 7.83 (0.6H, m), 7.34–7.09 (5H, m), 6.55 (1H, m), 4.90 (1H, m), 4.57 (1H, m), 4.11–3.99 (1.5H, m), 3.85–3.77 (0.8H, m), 3.63–3.59 (0.7H, m), 3.51–3.47 (0.6H, m), 3.08–2.95 (1.2H, m), 2.88–2.62 (1.2H, m), 2.57–2.49 (3H, m), 1.89–0.90 (25H, m). LRMS: +ve ion 508 [M+Na], –ve ion 484 [M–H].

Preparation of 2S-Amino-1-(4-benzyl-piperidin-1-yl)-3,3-dimethyl-butan-1-one (See Scheme 2)

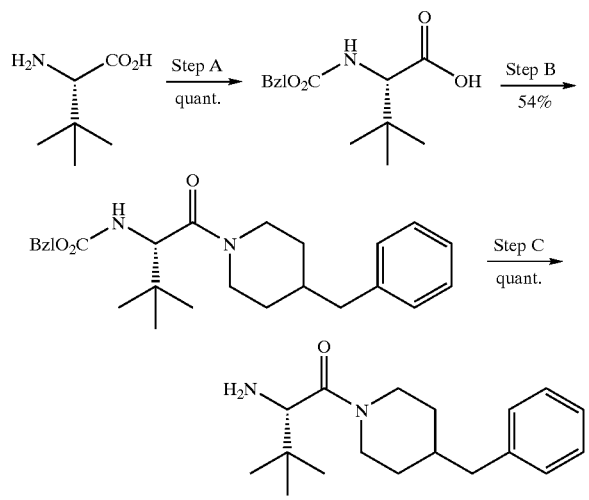

Reagents and conditions: A. NEt₃, N-(benzyloxycarbonyloxy)-succinimide, MeOH; B. EDCl, HOAt, DMF; C. cyclohexene, Pd/C, EtOH Step A: 2S-Benzyloxycarbonylamino-3,3-dimethyl-butyric Acid To a suspension of L-tert-leucine (11.88 g, 90.7 mmol) in methanol (200 ml) were added triethylamine (26.56 ml, 190 mmol) and N-(benzyloxycarbonyl-oxy)-succinimide (24.88 g, 99.8 mmol). The reaction mixture was stirred at room temperature for 14 h. Methanol was removed in vacuo to afford a viscous pale yellow oil, which was dissolved in ethyl acetate (100 ml). The organic layer was washed with 1M hydrochloric acid (15 ml) and brine, dried over anhydrous magnesium sulfate and filtered. The solvent was removed in vacuo to furnish the title compound as an oil (24 g, quant.). ¹H-NMR; δ(CDCl₃), 7.43–7.36 (5H, m), 5.36 (1H, d, J=9.4 Hz), 5.12 (2H, br s), 4.20 (1H, d, J=9.6 Hz) and 1.02 (9H, s). LRMS: +ve ion 266 [M+H], –ve ion 264 [M–H], 529 [2M–H].

Step B: 2S-[1-(4-Benzyl-piperidine-1 carbonyl)-2,2-dimethyl-propyl-carbamic Acid Benzyl Ester To a solution of 2S-Benzyloxycarbonylamino-3,3-dimethyl-butyric acid (923 mg, 3.48 mmol) and 4-benzyl piperidine (735 µl, 4.18 mmol) in DMF (16 ml) were added EDC (734 mg, 3.83 mmol) and HOAt (10 mg, 0.07 mmol). The reaction mixture was stirred for 14 h at room temperature. DMF was removed in vacuo and the crude residue was dissolved in ethyl acetate. The organic layer was washed with 1M hydrochloric acid (2×10 ml), water (10 ml), brine (10 ml), dried over anhydrous magnesium sulfate and filtered. Removal of the solvent in vacuo and purification by column chromatography (hexanes:ethyl acetate, 5:1) provided the desired amide (784 mg, 54%). ¹H-NMR; δ(CDCl₃), 7.36–7.14 (10H, m), 5.65 (1H, m), 5.17–5.05 (2H, m), 4.70–4.49 (2H, m), 2.96 (1H, m), 2.57–2.47 (2H, m), 1.90–1.59 (2H, m) and 1.38–0.87 (14H, m). LRMS: +ve ion 423 [M+H].

Step C: 2S-Amino-1-(4-benzyl-piperidin-1-yl)-3,3-dimethyl-butan-1-one

To a stirred solution of 2S-[1-(4-Benzyl-piperidine-1-carbonyl)-2,2-dimethyl-propyl-carbamic acid benzyl ester (784 mg, 1.86 mmol) in ethanol (4 ml) was added 10% palladium on charcoal (70 mg) and cyclohexene (380 µl, 3.71 mmol). The suspension was warmed to 75° C. for 1.5 h. The reaction mixture was filtered through celite and the solvent was removed in vacuo to afford quantitatively the title compound as a viscous oil. ¹H-NMR; δ(CDCl₃), 7.32–7.12 (5H, m), 4.69 (1H, m), 4.01 (1H, m), 3.53 (1H, m), 2.86 (1H, m), 2.63–2.45 (3H, m), 1.80–1.63 (3H, m), 1.30–1.08 (3H, m), 0.99 (4.5H, m) and 0.94 (4.5H, m). LRMS: +ve ion 289 [M+H].

EXAMPLES 2–12

The compounds of Examples 2–12 (Table 1) were prepared in array format using the generic procedure outlined below (see also Scheme 3).

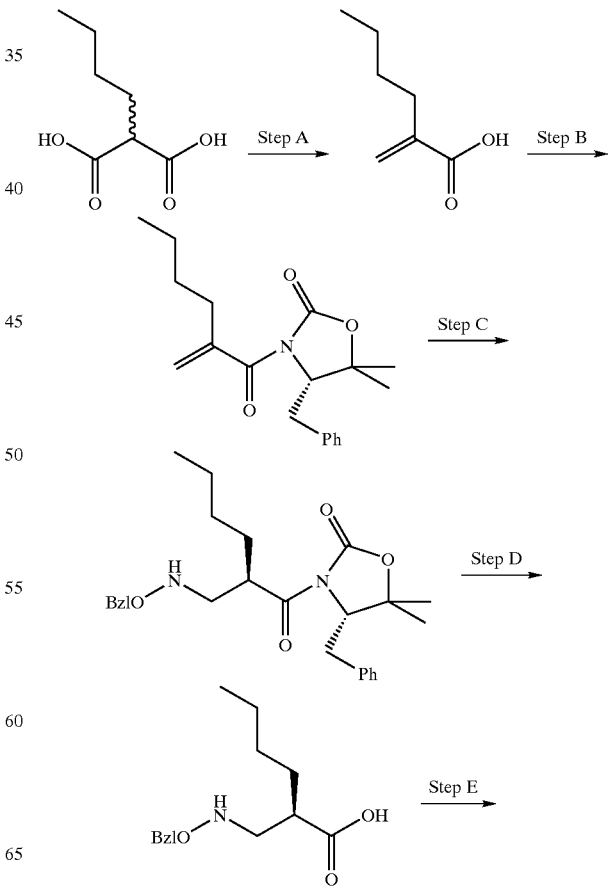

-continued

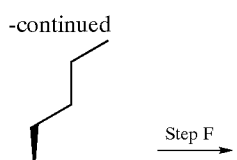

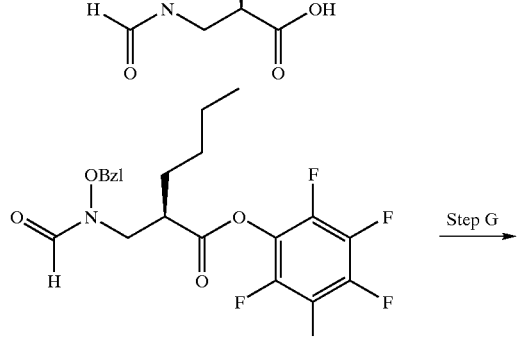

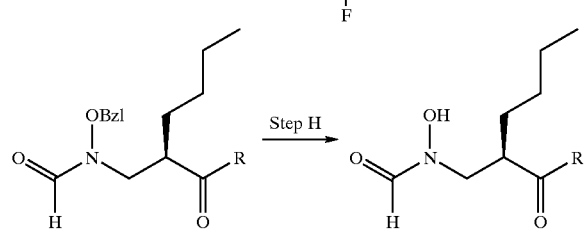

Reagents and conditions: A. piperidine, HCHO, EtOH, 80° C., o/n; B. ᵗBuCOCl, Et₃N then 3-lithio-4-benzyl-5,5-dimethyl-oxazolidin-2-one; C. H₂NOBzl, room temp., o/n then pTsOH, EtOAc; D. LiOH, aq THF, 0° C.; E. formic acetic anhydride, Et₃N, THF; F. PfpOH, EDC, HOBt, THF; G. Amine; H. cyclohexene, Pd/C, EtOH.

Analytical HPLC was performed on a Beckman System Gold, using Waters Nova Pak C18 column (150 mm, 3.9 mm) with 20 to 90% solvent B gradient (1 ml/min) as the mobile phase. [Solvent A: 0.05% TFA in 10% water 90% methanol; Solvent B: 0.05% TFA in 10% methanol 90%], detection wavelength at 230 nm. Preparative HPLC was performed on a Gilson autoprep instrument using a C18 Waters delta prep-pak cartridge (15 μm, 300 A, 25 mm, 10 mm) with 20 to 90% solvent B gradient (6 ml/min) as the mobile phase. [Solvent A water; Solvent B: methanol], UV detection was at 230 nm.

Step A: 2-Butyl Acrylic Acid

To a solution of n-butylmalonic acid (17.2 g, 107 mmol) in ethanol (200 ml) was added piperidine (12.76 ml, 129 mmol) and 37% aq. formaldehyde (40.3 ml, 538 mmol). The solution was heated to 80° C. during which time a precipitate appeared and gradually redissolved over 1 hour. The reaction mixture was stirred at 80° C. overnight then cooled to room temperature. The solvents were removed under reduced pressure and the residue was dissolved in ethyl acetate (200 ml), washed successively with 1 M hydrochloric acid and brine, dried over anhydrous magnesium sulfate and filtered. The filtrate was concentrated to give the title compound as a clear oil (13.37 g, 97%). $^1$H-NMR; δ (CDCl₃), 6.29 (1H, s), 5.65 (1H, s), 2.34–2.28 (2H, m), 1.54–1.26 (4H, m), 0.94 (3H, t, J=7.1 Hz).

Step B: 4S-Benzyl-3-(2-butyl-acryloyl)-5,5-dimethyl-oxazolidin-2-one

2-Butyl acrylic acid (21.5 g, 168 mmol) was dissolved in dry THF (500 ml) and cooled to −78° C. under a blanket of argon. Triethylamine (30 ml, 218 mmol) and pivaloyl chloride (21 ml, 168 mmol) were added at such a rate that the temperature remained below −60° C. The mixture was stirred at −78° C. for 30 minutes, warmed to room temperature for 2 hours and finally cooled back to −78° C.

In a separate flask, 4S-benzyl-5,5-dimethyl-oxazolidin-2-one was dissoved in dry THF (500 ml) and cooled to −78° C. under a blanket of argon. n-Butyllithium (2.4 M solution in hexanes, 83 ml, 200 mmol) was added slowly and the mixture was stirred for 30 minutes at room temperature. The resulting anion was tranferred via a cannula into the original reaction vessel. The mixture was allowed to warm to room temperature and was stirred overnight at room temperature. The reaction was quenched with 1 M potassium hydrogen carbonate (200 ml) and the solvents were removed under reduced pressure. The residue was partitioned between ethyl acetate and water. The organic layer was washed with brine, dried over anhydrous magnesium sulphate, filtered and concentrated under reduced pressure to give an orange oil. TLC analysis revealed the presence of unreacted chiral auxiliary in addition to the required product. A portion of the material (30 g) was dissolved in dichloromethane and flushed through a silica pad to give pure title compound as a yellow oil (25.3 g). $^1$H-NMR; δ (CDCl₃), 7.31–7.19 (5H, m), 5.41 (2H,s), 4.51 (1H, dd, J=9.7 & 4.2 Hz), 3.32 (1H, dd, J=14.2 & 4.2 Hz), 2.82 (1H, dd, J=14.2 & 9.7 Hz), 2.40–2.34 (2H, m), 1.48–1.32 (4H, m), 1.43 (3H, s), 1.27 (3H, s), 0.91 (3H, t, J=7.1 Hz). Some chiral auxiliary was recovered by flushing the silica pad with methanol.

Step C: 4S-Benzyl-3-[2-(benzyloxyamino-methyl)-hexanoyl]-5,5-dimethyl-oxazolidin-2-one (p-toluenesulfonic Acid Salt)

4S-Benzyl-3-(2-butyl-acryloyl)-5,5-dimethyl-oxazolidin-2-one (19.8 g, 62.8 mmol) was mixed with O-benzylhydroxylamine (15.4 g, 126 mmol) and stirred overnight at room temperature. The mixture was dissolved in ethyl acetate and the solution was washed with 1 M hydrochloric acid, 1 M sodium carbonate and brine, dried over anhydrous magnesium sulfate and filtered. The filtrate was concentrated under reduced pressure to afford a pale yellow oil (25.3 g) which was shown by NMR and HPLC analysis to contain 4S-benzyl-3-[2-(benzyloxyamino-methyl)-hexanoyl]-5,5-dimethyl-oxazolidin-2-one (ca. 82% d.e.) along with a trace of starting material. The product was combined with another batch (26.9 g, 76% d.e.) and dissolved in ethyl acetate (200 ml). p-Toluenesulfonic acid (22.7 g, 119 mmol) was added and the mixture was cooled to 0° C. The title compound was obtained as a white crystalline solid by seeding and scratching. Yield: 25.2 g, (34%, single diastereoisomer). A second crop (14.7 g, 20%, single diastereoisomer) was also obtained. $^1$H-NMR; δ (CDCl₃), 7.89 (2H, d, J=8.2 Hz), 7.37–7.12 (10H, m), 7.02 (2H, d, J=6.9 Hz), 5.28–5.19 (2H, m), 4.55 (1H, m), 4.23 (1H, m), 3.93 (1H, m), 3.58 (1H, m), 2.58 (1H, m), 2.35 (3H, s), 1.67–1.51 (2H, m), 1.29–1.16 (4H, m), 1.25 (3H, s), 1.11 (3H, s), 0.80–0.75 (3H, m).

Step D: 2R-(Benzyloxyamino-methyl)-hexanoic Acid

4S-Benzyl-3-[2R-(benzyloxyamino-methyl)-hexanoyl]-5,5-dimethyl-oxazolidin-2-one p-toluenesulfonic acid salt (25.2 g, 40.2 mmol) was partitioned between ethyl acetate and 1 M sodium carbonate. The organic phase was dried over anhydrous magnesium sulfate, filtered and evaporated under reduced pressure. The residual oil was dissolved in THF (150 ml) and water (50 ml), cooled to 0° C. and treated with lithium hydroxide (1.86 g, 44.2 mmol). The solution was stirred for 30 minutes at 0° C., then overnight at room temperature. The reaction was acidified to pH4 with 1 M citric acid and the solvents were removed. The residue was partitioned between dichloromethane and 1 M sodium carbonate. The basic aqueous layer was acidified to pH4 with 1M citric acid and extracted three times with ethyl acetate. The combined organic layers were dried over anhydrous magnesium sulfate, filtered and concentrated to provide the title compound as a colourless oil (7.4 g, 73%). $^1$H-NMR; δ (CDCl$_3$), 8.42 (2H, br s), 7.34–7.25 (5H, m), 4.76–4.66 (2H, m), 3.20–3.01 (2H, m), 2.73 (1H, m), 1.70–1.44 (2H, m), 1.34–1.22 (4H, m) and 0.92–0.86 (3H, m).

Step E: 2R-[(Benzyloxy-formylamino)-methyl)]-hexanoic Acid

To a solution of 2R-(Benzyloxyamino-methyl)-hexanoic acid (30.6 g, 0.12 mol) in dry THF (300 ml) was added formic acetic anhydride (26.8 ml, 0.31 mol) at 0° C. Triethylamine (18.5 ml, 0.13 mol) was added and the reaction was stirred for 1 h at 0° C. and 60 h at room temperature. The solvent was removed in vacuo to yield the title compound as a yellow oil (33.6 g, 99%) which was used in Step F without further purification. $^1$H-NMR; (CDCl$_3$, rotamers), 8.20–8.08 (0.7H, br s), 8.07–7.92 (0.3H, br s), 7.50–7.25 (5H, br m), 5.07–4.70 (2H, br m), 3.95–3.52 (2H, br m), 2.90–2.66 (1H, br s), 1.72–1.20 (6H, br m), 1.00–0.78 (3H, br s). LRMS: +ve ion 280 [M+1].

Step F: 2R-[(Benzyloxy-formyl-amino)-methyl]-hexanoic Acid pentafluoro-phenyl Ester To a solution of 2R-[(Benzyloxy-formylamino)-methyl)]-hexanoic acid (7.8 g, 19.9 mmol) in dry THF (500 ml) was added pentafluorophenol (44.3 g, 0.24 mol), EDC (27.7 g, 0.14 mol) and HOBt (16.2 g, 0.12 mol). The reaction was stirred overnight at room temperature. The solvent was removed in vacuo and the residue was dissolved in ethyl acetate, washed successively with 1 M sodium carbonate (3×500 ml) and water (1×500 ml), dried over anhydrous magnesium sulfate and filtered. The solvent was removed in vacuo to yield a yellow oil (60 g) that was purified by flash chromatography (5:1, hexane:ethyl acetate→1:2 hexane::ethyl acetate) to yield a clear oil (42.0 g, 79%). $^1$H-NMR; δ(CDCl$_3$, rotamers), 8.20–8.09 (0.7H, br s), 8.09–7.92 (0.3H, br s), 7.60–7.21 (5H, br m), 5.00–4.70 (2H, br m), 4.04–3.72 (2H, br m), 3.18–3.00 (1H, br s), 1.85–1.57 (2H, br m), 1.50–1.26 (4H, br m), 1.00–0.82 (3H, br m); LRMS: 466 [M+H].

Step G: Generic Experimental Procedure for the Synthesis of an Array of Amides

The coupling of amines to 2R-[(Benzyloxy-formylamino)-methyl]-hexanoic acid pentafluorophenyl ester was carried out on a Zymate XPII laboratory robot. To solutions of the pentafluorophenol ester (55.8 mg, 0.12 mmol) in dichloromethane (2 ml) were added individual amines (0.25 mmol) and the reaction mixtures were stirred at RT for 60 h. Purification was effected by removing excess amine and pentafluorophenol using scavenger resins. The pentafluorophenol was removed using a three fold excess (0.36 mmol) of A-26 carbonate resin (3.5 mmol loading). The resin was added to the reaction mixtures and agitated for 24 h, after which time it was filtered off. The excess amines were removed using a three-fold excess (0.36 mmol) of methylisocyanate polystyrene resin (1.2 mmol loading). The resin was added to the reaction mixtures and agitated for 4 h, after which time it was filtered off. The solvent was removed in vacuo using a Savant Speed Vac Plus to yield the coupled products. Yields were not calculated and the purity and integrity of each compound was verified using HPLC and LRMS.

Step H: Generic Transfer Hydrogenation Procedure

Products from Step G were individually taken up in an ethanol (2.7 ml) and cyclohexene (0.3 ml), 20% palladium on charcoal was added and the reactions stirred at 80° C. for 24 h. The Pd/C was filtered off and the solvent was removed in vacuo using a Savant Speed Vac Plus to yield the title compounds (examples 2–12, Table 1). Yields were not calculated and the purity and integrity of each compound were verified using HPLC and LRMS.

TABLE 1

| Example | Structure | Mass Spectral Data | HPLC | Purification |
| --- | --- | --- | --- | --- |
| 2 | 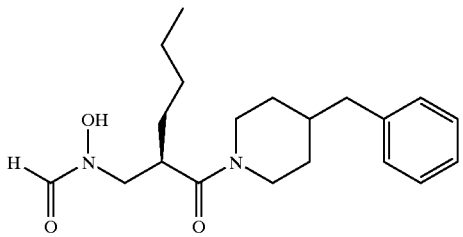 | 347 (M + 1, 100) | RT 18.5 min 100% | Resins |

TABLE 1-continued

| Example | Structure | Mass Spectral Data | HPLC | Purification |
|---------|-----------|--------------------|----|---------------|
| 3 | 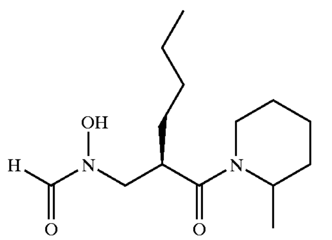 | 271 (M + 1, 100), 293 (M + Na, 50) | RT 19.4 min 100% | Resins |
| 4 | 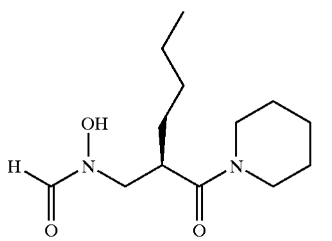 | 257 (M + 1, 50) | RT 24.4 min 100% | Resins |
| 5 | 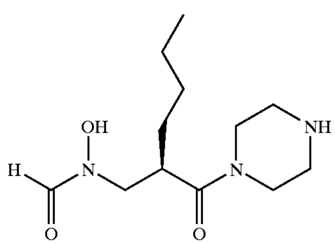 | 258 (M + 1, 100) | RT 3.1 min and 3.5 min | Resins, Prep HPLC |
| 6 | 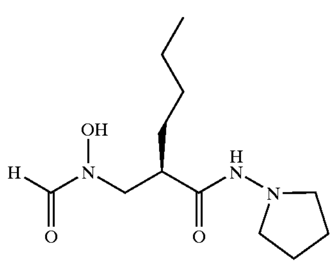 | 258 (M + 1, 100) | RT 4.0 min | Resins, Prep HPLC |
| 7 | 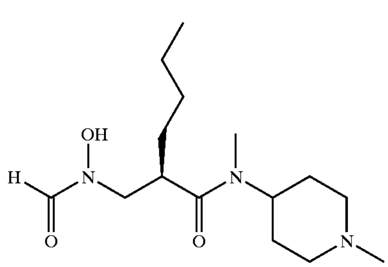 | 300 (M + 1, 100) | RT 4.2 min and 4.7 min (TFA salt) | Resins, Prep HPLC |

TABLE 1-continued

| Example | Structure | Mass Spectral Data | HPLC | Purification |
|---|---|---|---|---|
| 8 | 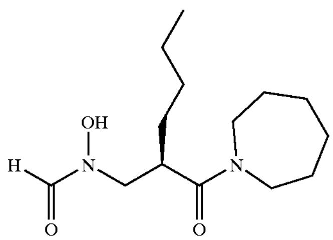 | 271 (M + 1, 100) | RT 18.5 min | Resins |
| 9 | 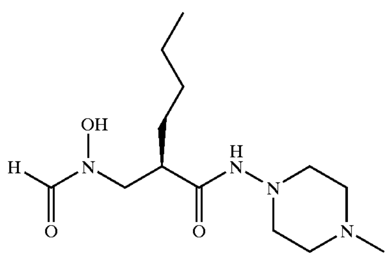 | 287 (M + 1, 100) | RT 3.0 min and 3.4 min | Resins, Prep HPLC |
| 10 | 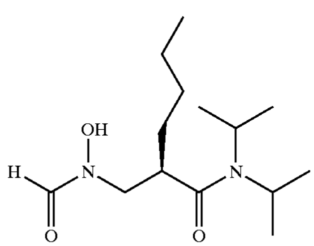 | 295 (M + 1, 100) | Only prep RT | Prep HPLC |
| 11 | 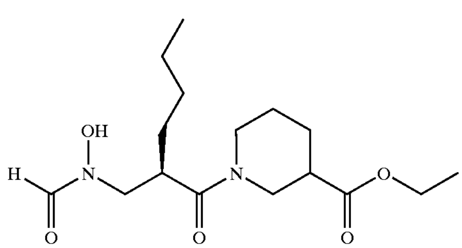 | 351 (M + Na, 100) | RT 7.6 min (grad 220 nm) | Ion exchange Prep HPLC |
| 12 | 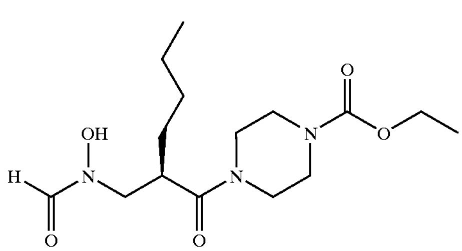 | 330 (M + 1, 100), 351 (M + Na, 50) | RT 16.8 min 100% | Resins |

EXAMPLE 13

2R,4-{2-[(Formyl-hydroxy-amino)-methyl]-hexanoyl}-1,1-dimethyl-piperazinium Iodide

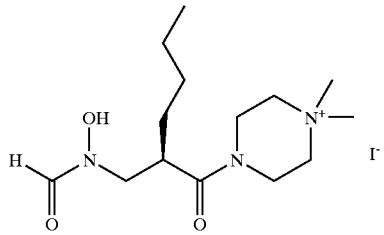

The title compound was prepared using the same procedure as for Examples 2 to 12, except for the final methylation (see Scheme 4)

Scheme 4

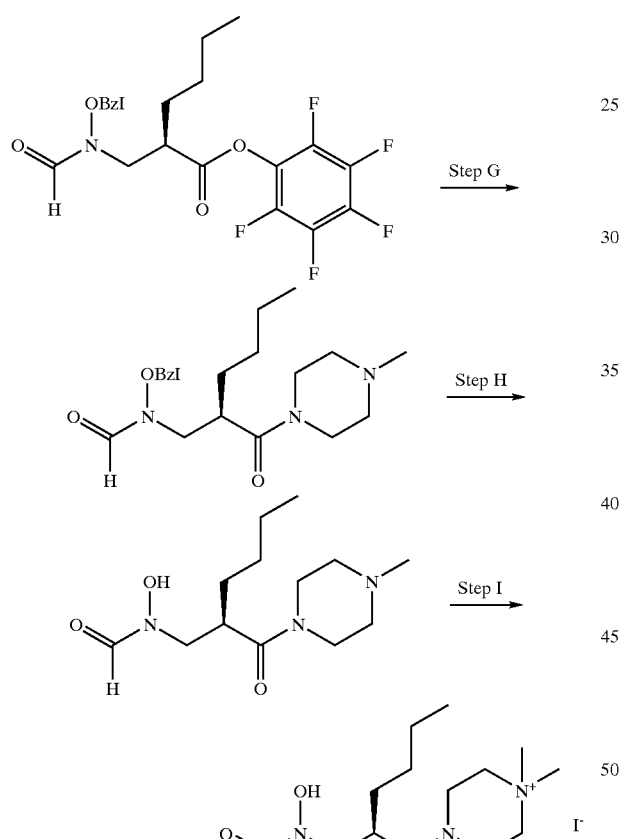

Reagents and conditions: G. N-methylpiperazine; H. H₂, Pd/C, EtOH; I. MeI, dry THF.

Step I: 2R,4-{2-[(Formyl-hydroxy-amino)-methyl]-hexanoyl}-1,1-dimethyl-piperazinium Iodide To a solution of N-hydroxy-N-[2R-(4-methyl-piperazine-1-carbonyl)-hexyl]-formamide (46 mg, 0.17 mmol) in anhydrous THF (5 ml) was added methyl iodide (22 µl, 0.34 mmol) dropwise at 0° C. The reaction mixture was stirred at 0° C. for 1 h and at room temperature for 18 h. The solvent was removed in vacuo to yield the title compound as a white hygroscopic solid (68 mg, 97%). $^1$H-NMR; CD$_3$OD, rotamers), 8.31 (0.7H, s), 7.88 (0.3H, s), 4.44–3.20 (17H, m), 1.75–1.20 (6H, m), 1.00–0.87 (3H, t, J=6.6 Hz). LRMS: +ve ion 286 [M].

The compounds of Examples 14–17 were prepared from 2R-[(benzyloxy-formyl-amino)-methyl]-hexyl pentafluorophenyl ester (Example 2) and the appropriate L-tert-leucine derivatives by analogy with the method described in Example 2.

EXAMPLE 14

2R-[(Formyl-hydroxy-amino)-methyl]-hexanoic Acid [2,2-dimethyl-1S-(piperidine-1-carbonyl)-propyl]-amide

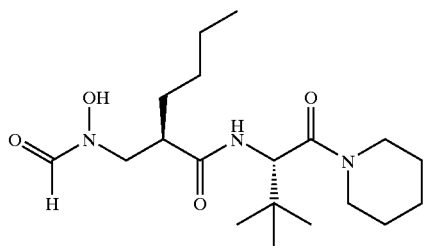

White foam. LRMS: +ve ion 392 [M+Na], −ve ion 368 [M−H]. HPLC: RT=20.7 min. (Purity 88%).

EXAMPLE 15

2R-[(Formyl-hydroxy-amino)-methyl]-hexanoic Acid [1S-(3,4-dihydro-1H-isoquinoline-2-carbonyl)-2,2-dimethyl-propyl]-amide

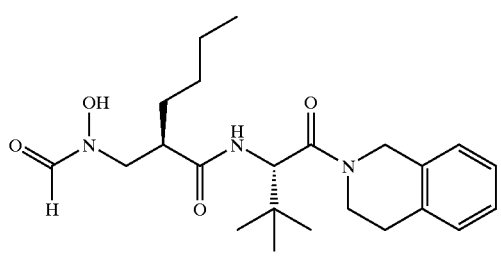

White foam: LRMS: +ve ion 440 [M+Na], −ve ion 416 [M−H]. HPLC: RT=20.7 min. (Purity 91%).

EXAMPLE 16

2R-[(Formyl-hydroxy-amino)-methyl]-hexanoic Acid [1S-(4-benzyl-4-hydroxy-piperidine-1-carbonyl)-2,2-dimethyl-propyl]-amide

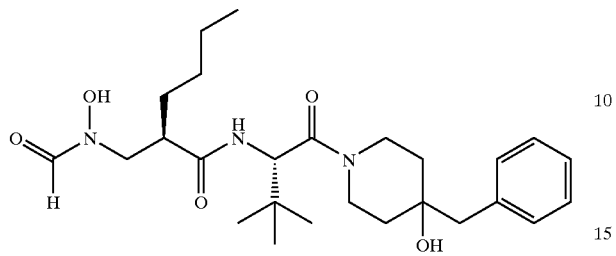

White foam. LRMS: +ve ion 498 [M+Na], −ve ion 474 [M−H]. HPLC: RT=21.0 min. (Purity 96%).

EXAMPLE 17

2R-[(Formyl-hydroxy-amino)-methyl]-hexanoic Acid [1S-(4-benzyl-piperazine-1-carbonyl)-2,2-dimethyl-propyl]-amide

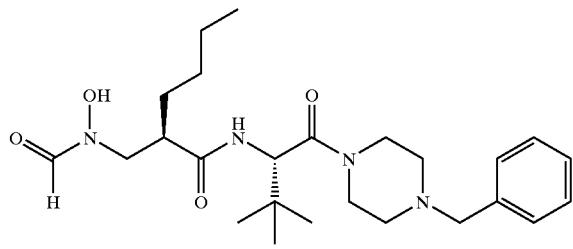

White foam. LRMS: +ve ion 461 [M+H]. HPLC: RT=16.6 min. (Purity 86%).

The compounds of Examples 18 to 25 were prepared by analogy with the method described in Example 2.

EXAMPLE 18

2R-[(Formyl-hydroxy-amino)-methyl]-hexanoic Acid (3-benzylsulfanyl-1S-dimethylcarbamoyl-propyl)-amide

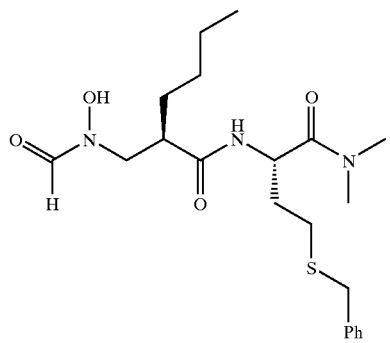

Pale yellow gum. $^1$H-NMR; δ (CDCl$_3$, rotamers), 8.39 (0.4H, s), 7.80 (0.6H, s), 7.27 (5H, m), 7.10 (0.4H, d, J=7.9 Hz), 6.97 (0.6H, d, J=8.3 Hz), 5.04 (1H, m), 4.03 (0.4H, dd, J=14.6 & 7.6 Hz), 3.73 (2.6H, m), 3.47 (1H, m), 3.06 (1.2H, s), 3.03 (1.8H, s), 2.94 (1.2H, s), 2.92 (1.8H, s), 2.78 (0.6H, m), 2.62 (0.4H, m), 2.40 (2H, m), 1.54 (8H, m) and 0.86 (3H, t, J=6.6 Hz). $^{13}$C-NMR; δ (CD$_3$OD, rotamers), 176.5, 176.2, 173.8, 173.7, 140.4, 130.4, 129.9, 128.5, 128.4, 53.9, 50.7, 49.9, 45.9, 45.8, 38.1, 37.3, 36.6, 32.8, 32.1, 31.4, 31.3, 30.7, 28.9, 28.8, 28.6, 24.1 and 14.7. LRMS: +ve ion 424 [M+H], 446 [M+Na].

EXAMPLE 19

3S-{2R-[(Formyl-hydroxy-amino)-methyl]-hexanoylamino}-N,N-dimethyl-succinamic Acid Benzyl Ester

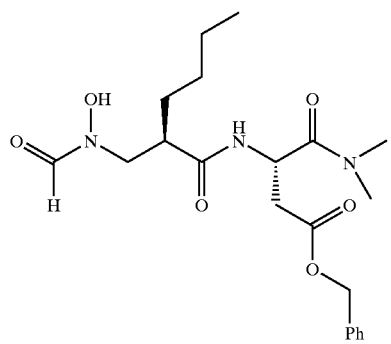

White solid. $^1$H-NMR; δ (CDCl$_3$, rotamers), 8.36 (0.3H, s), 7.79 (0.7H, s), 7.23 (6H, m), 5.30 (1H, m), 5.09 (2H, m), 3.96 (0.3H, dd, J=14.2 & 8.6 Hz), 3.71 (0.7H, dd, J=13.9 & 10.1 Hz), 3.47 (1H, m), 3.09 (1H, s), 3.06 (2H, s), 2.92 (1H, s), 2.91 (2H, s), 2.82 (3H, m), 1.68 (1H, m), 1.33 (5H, m) and 0.86 (3H, m). $^{13}$C-NMR; δ (CDCl$_3$, rotamers), 175.0, 173.1, 171.0, 170.7, 135.9, 129.0, 128.9, 128.8, 67.6, 67.3, 52.5, 49.2, 46.7, 46.4, 46.1, 45.9, 45.1, 37.7, 37.5, 37.4, 36.5, 36.4, 30.0, 29.8, 22.9 and 14.3. LRMS: +ve ion 444 [M+Na], 422 [M+H].

EXAMPLE 20

4S-Dimethylcarbamoyl-4-{2R-[(formyl-hydroxy-amino)-methyl]-hexanoylamino}-butyric Acid Benzyl Ester

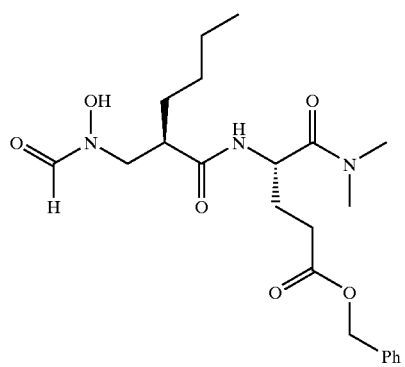

Pale yellow oil. LRMS: +ve ion 458 [M+Na], −ve ion 434 [M−H].

EXAMPLE 21

(5S-Dimethylcarbamoyl-5-{2R-[(formyl-hydroxy-amino)-methyl]-hexanoylamino}-pentyl)-dimethyl-ammonium Chloride

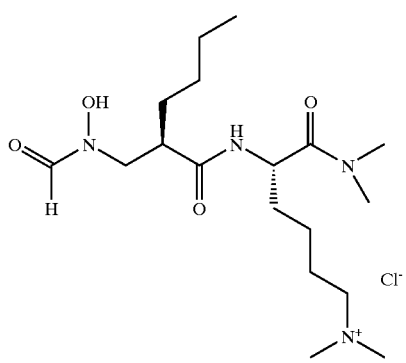

Yellow oil. $^1$H-NMR; δ (CDCl$_3$), 7.77 (1H, s), 7.45 (1H, d, J=8.9 Hz), 4.99 (1H, m), 3.81 (1H, m), 3.46 1H, m), 3.09 (6H, s), 2.98 (3H, m), 2.97 (3H, s), 2.95 (3H, s), 1.51 (12H, m) and 0.88 (3H, m). $^{13}$C-NMR; δ (CDCl$_3$), 173.6, 171.5, 158.8, 58.2, 53.6, 48.6, 45.4, 37.6, 36.2, 31.4, 30.2, 29.7, 24.7, 23.0, 22.5 and 14.3. LRMS: +ve ion 373 [M+H].

EXAMPLE 22

2R-[(Formyl-hydroxy-amino)-methyl]-butyric Acid (1S-carbamoyl-2,2-dimethyl-propyl)amide

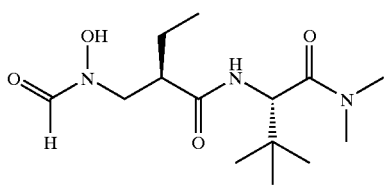

White hygroscopic solid. $^1$H-NMR; δ (CDCl$_3$), 9.29 (0.4H, S), 8.41 (0.4H, s), 7.84 (0.6H, s), 6.67 (0.4H, d, J=6.7 Hz), 6.52 (0.6H, d, J=10.1 Hz), 4.92–4.85 (1H, m), 4.05 (0.4H, dd, J=14.6 & 6.6 Hz), 3.84 (0.6H, dd, J=13.9 & 9.6 Hz), 3.59 (0.4H, dd, J=14.7 & 3.3 Hz), 3.50 (0.6H, dd, J=5.5 & 4.2 Hz), 3.16 (1.2H, s), 3.15 (1.8H, s), 2.98 (1.2H, s), 2.96 (1.8H, s), 2.72 (0.4H, m), 2.58 (0.6H, m), 1.68–1.42 (2H, m), 1.00–0.96 (9H, m) and 0.92–0.89 (3H, m).

$^{13}$C-NMR; δ (CDCl$_3$), 173.1, 55.5, 54.9, 51.7, 48.4, 48.0, 46.6, 38.9, 38.8, 36.3, 36.1, 31.3, 27.0, 26.9, 23.9, 23.8 and 12.1. LRMS: +ve ion 324 [M+Na] 300 [M–H].

EXAMPLE 23

2R-[(Formyl-hydroxy-amino)-methyl]-hexanoic Acid (1S-carbamoyl-2,2-dimethyl-propyl)amide

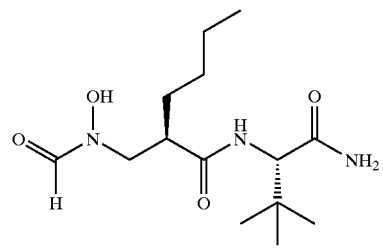

White powder. $^1$H-NMR; δ((CD$_3$)$_2$SO), 9.95 (0.4H, s), 9.50 (0.6H, s), 8.24 (0.4H, s), 7.79 (0.6H, s), 7.74 (1H, br m), 7.42 (1H, br s), 7.04 (1H, br s), 4.22 (1H, d, J=9.5 Hz), 3.69–3.26 (2H, m), 2.98–2.75 (1H, br m), 1.55–1.02 (6H, br m), 0.91 (9H, s) and 0.84 (3H, t, J=6.8 Hz). $^{13}$C-NMR; δ((CD$_3$)$_2$SO), 172.9, 172.4, 79.5, 60.0, 52.3, 48.7, 43.4, 43.2, 34.1, 29.8, 28.9, 27.1, 22.5 and 14.2. LRMS: +ve ion 324 [M+Na], 302 [M+H]. –ve ion 300 [M–H].

EXAMPLE 24

2R-[Formyl-hydroxy-amino)-methyl]-hexanoic Acid (1S-dimethyl-carbamoyl-4-guanidinobutyl)-amide

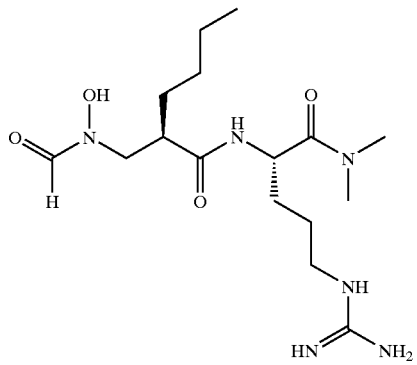

White powder. $^1$H-NMR; δ(CD$_3$OD, rotamers), 8.12 (0.1H, s), 7.60 (0.9H, s), 4.90 (1H, m), 3.67 (1H, dd, J=12.2, 12.2 Hz), 3.38 (1H, m), 3.22–3.09 (2H, m), 3.11 (3H, s), 3.02 (1H, m), 2.94 (3H, s), 1.74–1.47 (5H, m), 1.47–1.20 (5H, m) and 0.90 (3H, t, J=6.6 Hz). $^{13}$C-NMR; δ(CD$_3$OD, rotamers), 174.4, 172.0, 157.9, 55.9, 49.0, 45.0, 41.4, 37.7, 36.2, 30.6, 29.8, 29.7, 25.1, 23.2 and 14.4.

LRMS: +ve ion 373 [M+H].

EXAMPLE 25

[2R-(4-chlorophenyl)-3-(formyl-hydroxy-amino)-propionylamino]-2S-3,3,N,N-tetramethyl-butyramide

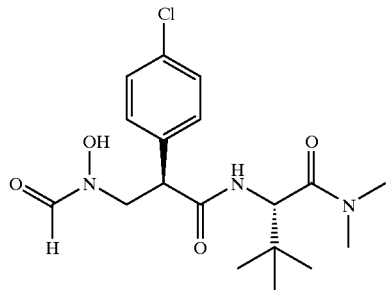

Colourless oil. $^1$H-NMR: $\delta$(CDCl$_3$, rotamers), 8.35 (0.25H, s), 7.78 (0.75H, s), 7.29 (4H, s), 7.08 (1H, d, J=9.4 Hz), 4.89 (1H, d, J=9.3 Hz), 4.28–4.07 (2H, m), 3.84 (0.25H, dd, J=13.3 & 3.5 Hz), 3.63 (0.75H, dd, J=13.1 & 4.4 Hz), 3.10 (1H, s), 3.07 (2H, s), 2.91 (1H, s), 2.88 (2H, s), 0.92 (9H, s); LRMS: +ve ion 384 [M+H].

EXAMPLE 26

2R-[(Formyl-hydroxy-amino)-methyl]-hexanoic Acid [2(3,4-dihydroxy-phenyl)-ethyl]-amide

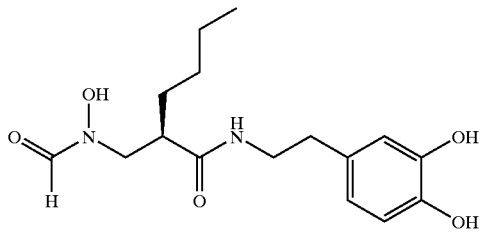

Yellow solid. $^1$H-NMR: $\delta$(CD$_3$OD, rotamers), 8.25 (0.3H, s), 8.08 (1H, m), 7.85 (0.7H, s), 6.68 (2H, m), 6.51 (1H, m), 3.70 (1H, m), 3.35 (3H, m), 2.80–2.50 (3H, m), 1.60–1.10 (6H, m) and 0.89 (3H, t, J=6.6 Hz); $^{13}$C-NMR: $\delta$(CD$_3$OD, rotamers), 176.5, 176.1, 146.7, 145.2, 132.3, 121.5, 117.8, 116.8, 60.7, 46.2, 46.1, 42.6, 36.3, 31.3, 30.8, 24.1 and 14.7; LRMS: +ve ion 325 [M+H], 347 [M+Na]; –ve ion 323 [M–H].

EXAMPLE 27

2R-[(Formyl-hydroxy-amino)-methyl]-hexanoic Acid [2(4-hydroxy-phenyl)-ethyl]-amide

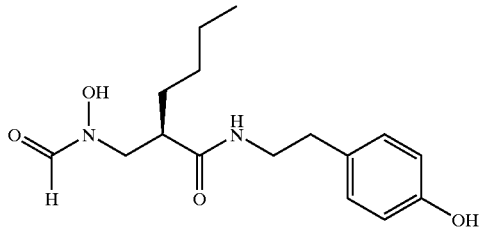

White solid. $^1$H-NMR: $\delta$(CD$_3$OD, rotamers), 8.24 (0.3H, s), 8.10 (1H, br m), 7.84 (0.7H, s), 7.03 (2H, d, J=8 Hz), 6.70 (2H, d, J=7 Hz), 3.68 (1H, m), 3.35 (3H, m), 2.70 (3H, m), 1.65–1.10 (6H, m) and 0.90 (3H, t, J=7.0 Hz); $^{13}$C-NMR: $\delta$(CD$_3$OD, rotamers), 176.5, 176.1, 157.3, 131.6, 131.2, 116.7, 53.9, 46.1, 45.1, 42.9, 36.1, 31.7, 31.2, 24.1 and 14.7, LRMS: +ve ion 309 [M+H], 331 [M+Na]; –ve ion 307 [M–H].

BIOLOGICAL EXAMPLE A

Demonstration of Antibacterial Effect a).

Minimal inhibitory concentrations (MIC) of inhibitors against *E. coli* strain DH5α (Genotype; F-φ80dlacZΔM15Δ (lacZYA-argF)U169 deoR recA1 endA1 hsdR17($r_k^-$,$m_k^+$) phoA supE44λ$^-$ thi-1 gyrA96 relA1) obtained from Gibco-BRL Life Technologies, *Enterobacter cloacae* (American Type Culture Collection number 13047), *Klebsiella pneumoniae* (American Type Culture Collection number 13883) or *Staphylococcus capitis* (American Type Culture Collection number 35661) were determined as follows. Stock solutions of test compound (Compounds 1 and 2 from Examples 1 and 2 respectively (both isomer A)) and three standard laboratory antibiotics, carbenicillin (Sigma, catalogue No. C3416), kanamycin (Sigma, catalogue No. K4000) and chloramphenicol (Sigma, catalogue No. C1919), were prepared by dissolution of each compound in dimethylsulfoxide at 10 mM. For the determination of the minimal inhibitory concentration, two fold serial dilutions were prepared in 2×YT broth (typtone 16 g/l, yeast extract 10 g/l, sodium chloride 5 g/l obtained from BIO 101 Inc, 1070 Joshua Way, Vista, Calif.92083, USA) to yield 0.05 ml compound-containing medium per well. Inocula were prepared from cultures grown overnight in 2×YT broth at 37° C. Cell densities were adjusted to absorbance at 660 nm (A$_{660}$)=0.1; the optical density-standardised preparations were diluted 1:1000 in 2×YT broth; and each well inoculated with 0.05 ml of the diluted bacteria. Microtitre plates were incubated at 37° C. for 18 hours in a humidified incubator. The MIC ($\mu$M) was recorded as the lowest drug concentration that inhibited visible growth. The compounds of the Examples inhibited bacterial growth. For example, the compound of Example 7 had an MIC against *E. coli* of 12.5 $\mu$M.

BIOLOGICAL EXAMPLE B i) Cloning of the *Escherichia coli* PDF Gene

The *E. coli* PDF gene was cloned in pET24a(+) (designated pET24-PDF) and was used to transform BL21 DE3 cells from Novagen Inc, (Madison, Wis.). Clones were selected at 37° C. on YT agar plates (8 g/l typtone, 5 g/yeast extract, NaCl 5 g/l, agar 15 g/l) supplemented with 30 $\mu$g/ml kanamycin.

ii) Expression of PDF

A 20 ml overnight culture of BL21 DE3 cells harbouring pET24-PDF was used to infect 500 ml 2×YT broth (16 g/l typtone, 10 g/l yeast extract, NaCl 5 g/l) containing 30 ug/ml kanamycin in a 2 liter baffled flask and grown at 37° C. with shaking to an OD$_{600}$ 0.6. The culture was then induced by adjusting the medium to 1.0 mM isopropyl β-D thiogalactopyranoside (IPTG). The induction was allowed to proceed for a further 3 hours at 37° C., the cells were harvested by centrifugation and the cell pellet washed with 250 ml phosphate buffered saline (PBS) and the pellet stored at –70° C.

iii) Preparation of Soluble Protein Fraction

The cells from a 1 liter expression were resuspeneded in 2×25 ml of ice cold phosphate buffered saline. The cell suspension was sonicated on ice using an MSE Soniprep 150 fitted with a medium probe and at an amplitude of 20–25 microns in 6×20 second pluses. The resulting suspension was then cleared by centrifugation at 20,000×g for 15 minutes. The supernatant was then used for further purification of the enzyme.

iv) PDF Purification

E. coli lysate from a 1 l culture in phosphate buffered saline (PBS) were adjusted to 2M ammonium sulphate. A 15 ml phenyl sepharose column was equilibrated with PBS/2M ammonium sulphate at 4° C. The lysate was loaded on the column and washed with equilibration buffer. The column was eluted by reducing the ammonium sulphate concentration from 2M to 0M over 10 column volumes. 5 ml fractions were collected and analysed by SDS-PAGE. The fractions containing the majority of the 20 kDa PDF were pooled. The pooled fractions were concentrated using a 3 kDa cutoff membrane to a volume of 5 ml. The fraction was then loaded onto a Superdex 75 (size exclusion chromatography) column equilibrated in PBS. The concentrated PDF pool eluted at one ml/min at 4° C. and 5 ml fractions collected and analysed by SDS-PAGE. The purest fractions were pooled and stored at −70° C.

(v) PDF In Vitro Assay

The assay was performed in a single 96 well plate in a final volume of 100 µl containing:

20 µl PDF (4 µg/ml)

20 µl 100 mM Hepes pH 7.0+1M KCl+0.05% Brij

10 µl serial dilution of test compound in 20% DMSO

50 µl formyl-Met-Ala-Ser (8 mM).

The assay was incubated at 37° C. for 30 minutes. The free amino group of the deformylated (Met-Ala-Ser) product was detected using fluorescamine, by the following additions:

50 µl 0.2M borate pH 9.5

50 µl fluorescamine (150 µg/ml in dry dioxane).

Fluorescence was quantified on SLT Fluostar plate reader using an excitation wavelength of 390 nM and an emission wavelength of 485 nM. Standard control reactions are a no inhibitor reaction which provides the zero inhibition figure and a no enzyme and a no inhibitor reaction which provides the 100% inhibition figure. The data was analysed by conversion of the fluorescence units to % inhibition and the inhibitor concentration plotted against % inhibition. The data was fitted to a sigmoidal function: $y=A+((B-A)/(1+((C/x)^D)))$, wherein A represents zero inhibition, B represents 100% inhibition and C represents the $IC_{50}$. D represents the slope. The $IC_{50}$ represents the concentration of inhibitor (nM) required to decrease enzyme activity by 50%.

The compounds of the invention were found to inhibit bacterial PDF in vitro.

What is claimed is:

1. A method of treating bacterial infections in humans and non-human mammals comprising administering an antibacterially effective amount of a compound selected from the group consisting of N-[3S-(4-benzylpiperidine-1-carbonyl)-2,2-dimethyl-propyl]-3-cyclopentyl-2R[(formyl-hydroxy-amino)-methyl]-propionamide, N-[2R-(4-benzyl-piperidine-1-carbonyl)-hexyl]-N-hydroxy-formamide, N-hydroxy-N-[2R-(2-methyl-piperidine-1-carbonyl)-hexyl]-formamide, N-hydroxy-N-[2R-(piperidine-1-carbonyl)-hexyl]-formamide, N-hydroxy-N-[2R-(piperazine-1-carbonyl)-hexyl]-formamide, 2R-[(formyl-hydroxy-amino)-methyl]-hexanoic acid pyrrolidin-1-ylamide, 2R-[(formyl-hydroxy-amino)-methyl]-hexanoic acid methyl-(1-methylpiperidin-4-yl)-amide, N-[2R-(azepane-1-carbonyl)-hexyl]-N-hydroxy-formamide, 2R-[(formyl-hydroxy-amino)-methyl]-hexanoic acid (4-methyl-piperazin-1-yl)-amide, 2R-[(formyl-hydroxy-amino)-methy]-hexanoic acid diisopropylamide, 1-{2R-[(formyl-hydroxy-amino)-methyl]-hexanoyl}-piperidine-3-carboxylic acid ethyl ester, 4-{2R-[(formyl-hydroxy-amino)-methyl]-hexanoyl}-piperazine-1-carboxylic acid ethyl ester, 4-{2R-[(formyl-hydroxy-amino)-methyl]-hexanoyl}-1,1-dimethyl-piperazinium iodide, 2R-[(Formyl-hydroxy-amino)-methyl]-hexanoic acid [2,2-dimethyl-1 (piperidine-1-carbonyl)-propyl]-amide, 2R-[(formyl-hydroxy-amino)-methyl]-hexanoicacid [1S-(3,4-dihydro-1H-isoquinoline-2-carbonyl)-2,2-dimethyl-propyl]-amide, 2R-[(formyl-hydroxy-amino)-methyl]-hexanoic acid [1S-(4-benzyl-4-hydroxy-piperidine-1-carbonyl)-2,2-dimethyl-propyl]-amide, 2R-[(formyl-hydroxy-amino)-methyl]-hexanoic acid [1S-(4-benzyl-piperazine-1-carbonyl)-2,2-dimethyl-propyl]-amide, 2R-[(formyl-hydroxy-amino)-methyl]-hexanoic acid (3-benzylsulfanyl-1S-dimethylcarbamoyl-propyl)-amide, 3S-{2R-[(formyl-hydroxy-amino)-methyl]-hexanoylamino}-N,N-dimethyl-succinamic acid benzyl ester, 4S-dimethylcarbamoyl-4-{2R-[(formyl-hydroxy-amino)-methyl]-hexanoyamino-butyric acid benzyl ester, (5S-dimethylcarbamoyl-5-{2R-[(formyl-hydroxy-amino)-methyl]-hexanoylamino}-pentyl)-dimethyl-ammonium chloride, 2R-[(formyl-hydroxy-amino)-methyl]-butyric acid (1-carbamoyl-2,2-dimethylpropyl)amide, 2-[(formyl-hydroxy-amino)-methyl]-hexanoic acid (1-carbamoyl-2,2-dimethylpropyl)amide, 2R-[formyl-hydroxy-amino)-methyl]-hexanoic acid (1-dimethyl-carbamoyl-4-guanidinobutyl)-amide, 2R-[2-(4-chlorophenyl)-3-(formyl-hydroxy-amino)-propionylamino]-2S-3,3,N,N-tetramethyl-butyramide, 2R-[(formyl-hydroxy-amino)-methyl]-hexanoic acid [2(3,4-dihydroxy-phenyl)-ethyl]-amide, 2R-[(formyl-hydroxy-amino)-methyl]-hexanoic acid [2(4-hydroxyphenyl)-ethyl]-amide, or pharmaceutically and veterinarily acceptable salts, hydrates or solvates thereof.

2. The method of claim 1 wherein the compound is applied to the site of contamination.

* * * * *